(12) United States Patent
Lewandowski et al.

(10) Patent No.: US 7,576,144 B2
(45) Date of Patent: *Aug. 18, 2009

(54) DENTAL COMPOSITIONS CONTAINING CARBOSILANE MONOMERS

(75) Inventors: Kevin M. Lewandowski, Inver Grove Heights, MN (US); Ahmed S. Abuelyaman, Woodbury, MN (US); Babu N. Gaddam, Woodbury, MN (US); Sumita B. Mitra, West St. Paul, MN (US); Brian N. Holmes, St. Paul, MN (US); Adrian S. Eckert, Munich (DE); Peter Bissinger, Diessen (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/571,944

(22) PCT Filed: Jul. 13, 2005

(86) PCT No.: PCT/US2005/024826

§ 371 (c)(1),
(2), (4) Date: Aug. 2, 2007

(87) PCT Pub. No.: WO2006/019801

PCT Pub. Date: Feb. 23, 2006

(65) Prior Publication Data

US 2007/0276059 A1 Nov. 29, 2007

Related U.S. Application Data

(60) Provisional application No. 60/587,762, filed on Jul. 14, 2004.

(51) Int. Cl.
*A61K 6/083* (2006.01)
(52) U.S. Cl. .................. 523/115; 523/116; 528/26; 528/32; 433/228.1
(58) Field of Classification Search ................ 523/115, 523/116
See application file for complete search history.

(56) References Cited

U.S. PATENT DOCUMENTS

| 3,159,601 | A | 12/1964 | Ashby |
| 3,220,972 | A | 11/1965 | Lamoreaux |
| 3,419,593 | A | 12/1968 | Willing |
| 3,715,334 | A | 2/1973 | Karstedt |
| 3,775,352 | A | 11/1973 | Leonard, Jr. |
| 3,775,452 | A | 11/1973 | Karstedt |
| 3,814,730 | A | 6/1974 | Karstedt |
| 3,927,116 | A | 12/1975 | Rick et al. |
| 3,933,880 | A | 1/1976 | Bergstrom et al. |
| 3,971,754 | A | 7/1976 | Jurecic |
| 4,071,424 | A | 1/1978 | Dart et al. |
| 4,288,345 | A | 9/1981 | Ashby et al. |
| 4,356,296 | A | 10/1982 | Griffith et al. |
| 4,391,590 | A | 7/1983 | Dougherty |
| 4,421,903 | A | 12/1983 | Ashby |
| 4,503,169 | A | 3/1985 | Randklev |
| 4,510,094 | A | 4/1985 | Drahnak |
| 4,530,879 | A | 7/1985 | Drahnak |
| 4,600,484 | A | 7/1986 | Drahnak |
| 4,603,215 | A | 7/1986 | Chandra et al. |
| 4,642,126 | A | 2/1987 | Zador et al. |
| 4,652,274 | A | 3/1987 | Boettcher et al. |
| 4,665,217 | A | 5/1987 | Reiners et al. |
| 4,695,251 | A | 9/1987 | Randklev |
| 4,705,765 | A | 11/1987 | Lewis |
| 4,706,765 | A | 11/1987 | Lee et al. |
| 4,752,338 | A | 6/1988 | Reiners et al. |
| 4,767,798 | A | 8/1988 | Gasser et al. |
| 4,771,530 | A | 9/1988 | Creedon |
| 4,772,530 | A | 9/1988 | Gottschalk et al. |
| 4,788,268 | A | 11/1988 | Lau et al. |
| 4,874,450 | A | 10/1989 | Gottschalk et al. |
| 4,882,365 | A | 11/1989 | Gasser et al. |
| 4,954,414 | A | 9/1990 | Adair et al. |
| 5,026,902 | A | 6/1991 | Fock et al. |
| 5,055,372 | A | 10/1991 | Shanklin et al. |
| 5,057,393 | A | 10/1991 | Shanklin et al. |
| 5,076,844 | A | 12/1991 | Fock et al. |
| 5,145,886 | A | 9/1992 | Oxman et al. |
| 5,165,890 | A | 11/1992 | Discko, Jr. |
| 5,233,006 | A | 8/1993 | Wolter et al. |
| 5,322,440 | A | 6/1994 | Steele |
| 5,346,980 | A | 9/1994 | Babu |
| 5,399,738 | A | 3/1995 | Wolter et al. |

(Continued)

FOREIGN PATENT DOCUMENTS

EP 0 173 567 A2 3/1986

(Continued)

OTHER PUBLICATIONS

ANSI/ADA specification No. 27 (1993).
Beck et al., Phenenyl Silicon Compounds, *J. Chem. Eng. Data*, 1963, 8(3), 453-454.
Houben-Weyl, *Methoden der Organischen Chemie*, vol. VI/3, pp. 56, 57, Georg Thieme Verlag, Stuttgart, 1965, 4th Edition.
Houben-Weyl, *Methoden der Organischen Chemie*, vol. XIII/2a, pp. 47-192, Georg Thieme Verlag, Stuttgart, 1973, 4th Edition.
ISO 4049.
ISO 9917.

(Continued)

*Primary Examiner*—Tae H Yoon
(74) *Attorney, Agent, or Firm*—Dean A. Ersfeld

(57) ABSTRACT

Carbosilane monomers that include the following structural features: at least two Si-arylene bonds; at least one (meth)acrylate moiety; no Si—O bonds; and preferably at least two silicon atoms.

6 Claims, No Drawings

U.S. PATENT DOCUMENTS

| | | | |
|---|---|---|---|
| 5,532,398 | A | 7/1996 | Wolter et al. |
| 5,545,676 | A | 8/1996 | Palazzotto et al. |
| 6,046,250 | A | 4/2000 | Boardman et al. |
| 6,245,828 | B1 | 6/2001 | Weinmann et al. |
| 6,376,569 | B1 | 4/2002 | Oxman et al. |
| 6,387,981 | B1 | 5/2002 | Zhang et al. |
| 6,562,953 | B2 | 5/2003 | Dhainaut et al. |
| 6,566,413 | B1 | 5/2003 | Weinmann et al. |
| 6,572,693 | B1 | 6/2003 | Wu et al. |
| 6,624,211 | B2 | 9/2003 | Karim et al. |
| 6,624,236 | B1 | 9/2003 | Bissinger et al. |
| 6,653,375 | B2 | 11/2003 | Moszner et al. |
| 6,852,822 | B1 | 2/2005 | Bissinger et al. |
| 2002/0013454 | A1 | 1/2002 | Dhainaut et al. |
| 2002/0115743 | A1 | 8/2002 | Karim et al. |
| 2003/0035899 | A1 | 2/2003 | Klettke et al. |
| 2003/0152601 | A1 | 8/2003 | Kanayama |
| 2003/0166816 | A1 | 9/2003 | Bissinger et al. |
| 2003/0181541 | A1 | 9/2003 | Wu et al. |
| 2003/0236342 | A1 | 12/2003 | Walz et al. |
| 2004/0082683 | A1 | 4/2004 | Karim et al. |
| 2004/0186202 | A1 | 9/2004 | Klettke et al. |
| 2004/0209990 | A1 | 10/2004 | Walz et al. |
| 2005/0013842 | A1* | 1/2005 | Qiu et al. .................. 424/423 |
| 2005/0252413 | A1 | 11/2005 | Kangas et al. |
| 2005/0252414 | A1 | 11/2005 | Craig et al. |
| 2005/0256223 | A1 | 11/2005 | Kolb et al. |
| 2008/0045626 | A1* | 2/2008 | Lewandowski et al. ..... 523/105 |

FOREIGN PATENT DOCUMENTS

| | | |
|---|---|---|
| EP | 0 201 031 A2 | 11/1986 |
| EP | 0 201 778 A1 | 11/1986 |
| EP | 0 238 025 A2 | 9/1987 |
| EP | 0 238 025 A3 | 9/1987 |
| EP | 0 201 778 B1 | 12/1988 |
| EP | 0 201 031 B1 | 8/1989 |
| EP | 0 373 384 A1 | 6/1990 |
| EP | 0 451 709 A2 | 10/1991 |
| EP | 0 373 384 B1 | 10/1992 |
| EP | 0 238 025 B1 | 12/1992 |
| EP | 0 661 331 A2 | 7/1995 |
| EP | 0 451 709 B1 | 12/1999 |
| EP | 1 368 402 A1 | 12/2003 |
| EP | 1 368 402 B1 | 8/2004 |
| WO | WO 86/01219 A1 | 2/1986 |
| WO | 00/38619 A2 | 7/2000 |
| WO | 00/38619 A3 | 7/2000 |
| WO | 00/42092 A1 | 7/2000 |
| WO | 01/07444 A1 | 2/2001 |
| WO | 01/30305 A1 | 5/2001 |
| WO | 01/30306 A1 | 5/2001 |
| WO | 01/30307 A1 | 5/2001 |
| WO | 01/92271 A1 | 12/2001 |
| WO | 01/92281 A1 | 12/2001 |
| WO | 01/95862 A1 | 12/2001 |
| WO | 01/95865 A1 | 12/2001 |
| WO | 02/066535 A1 | 8/2002 |
| WO | 03/063804 A1 | 8/2003 |
| WO | 2006/005363 A1 | 1/2006 |
| WO | 2006/005366 A1 | 1/2006 |
| WO | 2006/019796 | 2/2006 |
| WO | 2006/019801 | 2/2006 |

OTHER PUBLICATIONS

Tarbell et al., The Rearrangement of 4-Crotyloxy-3,5-Dichlorobenzoic Acid, *J. Am. Chem. Soc.*, 1942, 64(5), 1066-1070.

Marciniec, *Comprehensive Handbook on Hydrosilylation*, pp. 8ff, 107ff, and 151ff, Pergamon Press, Oxford, 1992.

Watts shrinkage test procedure (3M test method DTS-1303).

Watts et al., Kinetic Measurement of Photo-Polymerization Contraction in Resins and Composites, *Meas. Sci. Technol.*, 2, 788-794 (1991).

U.S. Appl. No. 09/541,417 (Karim) "Dental Materials with Extendable work Time Kits, and Methods," filed Apr. 3, 2000.

U.S. Appl. No. 60/587,978 "Dental Compositions Containing Carbosilane Polymers," filed Jul. 14, 2004.

Tsumura, Manabu, et al., "Synthesis and Properties of Polycarbosilanes with the Meta-Linkage Bending Unit by Hydrosilylation Polymerization", Table 1, Oct. 25, 1996, pp. 3156-3157 and Journal of Polymer Science, Part A: Polymer Chemistry, 3155-3161 34(15).

* cited by examiner

DENTAL COMPOSITIONS CONTAINING CARBOSILANE MONOMERS

CROSS REFERENCE TO RELATED APPLICATIONS

This application is a national stage filing under 35 U.S.C. 371 of PCT/US2005/024826 filed Jul. 13, 2005, which claims the benefit of U.S. Provisional Application No. 60/587,762, filed Jul. 14, 2004, the disclosure of which is incorporated by reference in its entirety herein.

FIELD OF THE INVENTION

Carbosilane monomers and dental compositions comprising carbosilane monomers.

BACKGROUND

It is well known that the volume shrinkage of dental compositions upon curing results in high stress and micro fractures in the composite. Such defects may lead to clinical failure of the composite material. Therefore, it is important to develop dental composites with a reduced volume shrinkage while maintaining the outstanding physical properties of current materials.

Current commercial (meth)acrylate-based composites exhibit a volume shrinkage of 2-4 percent (%) upon polymerization. The goal is to reduce the shrinkage below 2% while maintaining other desirable physical properties, such as compressive strength and viscosity. Although many types of components have been developed for addition to (meth)acrylate-based composites that reduce polymerization shrinkage, composites based on them generally suffer from reduced physical properties compared to commercial products, such as that available from 3M Company, St. Paul, Minn. under the trade designation FILTEK Z250.

Thus, there is still a need for new components that can be added to (meth)acrylate-based dental compositions that provide reduced shrinkage.

SUMMARY OF THE INVENTION

The present invention provides carbosilane monomers for use in (meth)acrylate-based dental compositions. The carbosilane monomers (i.e., carbosilane-containing monomers) preferably include the following structural features: at least 2 Si-arylene bonds; at least 1 (meth)acrylate moiety; no Si—O bonds; and preferably at least 2 silicon atoms. In certain embodiments, the carbosilane monomers are formed from the reaction of aromatic silanes and ethylenically unsaturated building blocks. Dental compositions that include these materials typically have a lower volume shrinkage upon hardening. Also, the resultant hardened composites have potentially higher stain resistance compared to current composites.

The compositions can also include an initiator system, such as a photoactive free radical source (preferably one activated by blue light). In certain embodiments, dental compositions also include a filler system, preferably up to 80 percent by weight (i.e., wt-%) of a filler system (preferably including an inorganic filler), based on the total weight of the composition. Other optional ingredients include, for example, a colorant, a flavoring agent, a medicament, a stabilizer, a viscosity modifier, a diluting agent, a flow control additive, an antimicrobial, a thixotropic agent, and a polymeric thickener.

Various combinations of each of the components listed herein can be used for desired effect.

In one embodiment, the present invention provides a dental composition that includes a carbosilane-containing monomer having the following (Formula I):

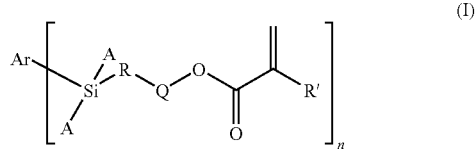

wherein:
Ar is an arylene group;
each A is independently an aliphatic, cycloaliphatic, aromatic group, or combinations thereof;
each R is independently an aliphatic group, cycloaliphatic group, or combinations thereof, optionally including one or more O, Br, Cl, or Si atoms, or combinations thereof, which can include a bicyclic group;
each Q is independently a bond, or an aliphatic group, cycloaliphatic group, aromatic group, or combinations thereof, optionally including one or more O, Br, Cl, or Si atoms, or combinations thereof, which can include a bicyclic group;
each R' is independently hydrogen or methyl; and
n is at least 2.

Definitions

By "crystallizable" it is meant that the material either alone or in the presence of other monomers displays a crystalline melting point at 20° C. or above when measured by differential scanning calorimetry (DSC). The peak temperature of the observed endotherm is taken as the crystalline melting point. The crystalline phase includes multiple lattices in which the material assumes a conformation in which there is a highly ordered registry in adjacent chemical moieties of which the material is constructed. The packing arrangement (short order orientation) within the lattice is highly regular in both its chemical and geometric aspects. A crystallizable component may be in a "semicrystalline state" in that long segments of polymer chains appear in both amorphous and crystalline states or phases at 20° C. or above. Thus, herein a "crystallizable" component encompasses semicrystalline materials.

The term "non-crystallizable" means materials that are composed of randomly orientated atoms, ions, or molecules that do not form defined patterns, lattice structures, or long range order (i.e., amorphous). Non-crystallizable materials do not display a crystalline melting point at 20° C. or above when measured by differential scanning calorimetry (DSC).

The term "hardenable" refers to a material that can be cured or solidified, e.g., by heating to remove solvent, heating to cause polymerization, chemical crosslinking, radiation-induced polymerization or crosslinking, or the like.

The term "arylene" as used herein includes carbocyclic aromatic rings or ring systems, wherein the aromatic rings can be optionally bridged by oxygen, nitrogen, sulfur, or alkylene groups, or combinations thereof, and optionally substituted with halogen, alkyl or alkoxy groups, or combinations thereof. Examples of arylene groups include phenylene, naphthylene, biphenylene, fluorenylene, indenylene, diphenylene ether, optionally substituted with alkyl and/or alkoxy groups.

The terms "comprises" and variations thereof do not have a limiting meaning where these terms appear in the description and claims.

As used herein, "a," "an," "the," "at least one," and "one or more" are used interchangeably. Thus, for example, a dental composition that comprises "a" carbosilane-containing monomer can be interpreted to mean that the dental composition includes "one or more" carbosilane-containing monomers. Similarly, a composition comprising "a" filler can be interpreted to mean that the composition includes "one or more" types of fillers.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides carbosilane monomers for use in (meth)acrylate-based dental compositions. The carbosilane monomers (i.e., carbosilane-containing monomers) preferably include the following structural features: at least 2 Si-arylene bonds; at least 1 silicon atom; at least 1 (meth) acrylate moiety; no Si—O bonds; and preferably at least 2 silicon atoms. The term "arylene" as used herein includes carbocyclic aromatic rings or ring systems. The carbosilane monomer is capable of polymerizing, and optionally crosslinking, due to preferred multi-functionality.

Significantly, these aromatic carbosilane monomers can be prepared using simple hydrosilation procedures, for example. The wide availability of starting materials (e.g., aromatic silanes and (meth)acrylate functional olefins) allows for broad control over the structure, architecture, and functionality of the carbosilane monomer. Through this chemistry, it is possible to prepare, preferably in one step, monomeric materials with polymerizable functionality (preferably, (meth) acrylate functionality).

Carbosilane Monomer and Preparation Thereof

The carbosilane monomers typically include multiple functionality. The molecular weight and viscosity of the monomeric material can be easily controlled by simply changing the building blocks used in the reaction. The number average molecular weight of the carbosilane materials may vary over a broad range. Preferably, the molecular weight is less than 1000 grams per mole (g/mol).

A preferred carbosilane monomer is hardenable (e.g., polymerizable and/or crosslinkable), preferably by a free radical mechanism. Such carbosilane materials preferably include the following structural features: at least 2 Si-arylene bonds; at least 1 silicon atom; at least 1 (meth)acrylate moiety; and no Si—O bonds. Preferably, the carbosilane monomer has a functionality greater than one, more preferably at least two.

A preferred class of carbosilane monomers are of the following Formula I:

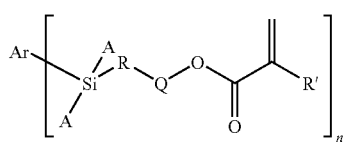

(I)

wherein:
Ar is an arylene group;
each A is independently an aliphatic, cycloaliphatic, aromatic group, or combinations thereof;
each R is independently an aliphatic group, cycloaliphatic group, or combinations thereof, optionally including one or more O, Br, Cl, or Si atoms, or combinations thereof, which can include a bicyclic group;
each Q is independently a bond, or an aliphatic group, cycloaliphatic group, aromatic group, or combinations thereof, optionally including one or more O, Br, Cl, or Si atoms, or combinations thereof, which can include a bicyclic group;
each R' is independently hydrogen or methyl; and
n is at least 2 (preferably, 2-10, more preferably, 2-6, and even more preferably 2-3).

The term "arylene" as used herein includes carbocyclic aromatic rings or ring systems, wherein the aromatic rings can be optionally bridged by oxygen, nitrogen, sulfur, or alkylene groups, or combinations thereof, and optionally substituted with halogen, alkyl or alkoxy groups, or combinations thereof. Examples of arylene groups include phenylene, naphthylene, biphenylene, fluorenylene, indenylene, diphenylene ether, optionally substituted with alkyl and/or alkoxy groups.

Preferably, Ar is an arylene group having 6-14 carbon atoms in the ring system, optionally substituted by halogen, alkyl groups (preferably having 1-10 carbon atoms, and more preferably 1-6 carbon atoms), or alkoxy groups (preferably having 1-10 carbon atoms, and more preferably having 1-6 carbon atoms), or combinations thereof.

Preferably, each A is independently an aliphatic group having 1-6 carbon atoms, cycloaliphatic group having 1-6 carbon atoms, an aromatic group having 6-14 carbon atoms, or combinations thereof. More preferably, each A is independently an aliphatic group having 1-6 carbon atoms (and more preferably, 1-3 carbon atoms).

Preferably, each R is independently an aliphatic group having 1-10 carbon atoms, cycloaliphatic group having 3-10 carbon atoms, or combinations thereof. More preferably, each R is independently an alkylene group having 2-10 carbon atoms.

Preferably, each Q is independently an aliphatic group having 1-10 carbon atoms, cycloaliphatic group having 3-10 carbon atoms, aromatic group having 6-10 carbon atoms, or combinations of such groups, optionally including one or more O, Br, Cl, or Si atoms, or combinations thereof. More preferably, each Q is independently an (C1-C3)alkylene, oxy (C1-C3)alkylene group, or a (C3-C9)cycloaliphatic group.

The carbosilane monomer can be formulated into dental composites that exhibit a total volumetric polymerization shrinkage of no greater than 2.0% (typically, a shrinkage of 1.4% to 2.0%), wherein the percentage is based on the volume of the composition prior to hardening, preferably while maintaining excellent physical properties.

Preferably, the total amount of the carbosilane monomer in the dental composition is at least 1 wt-%, more preferably, at least 3 wt-%, and most preferably, at least 5 wt-%, based on the total weight of the composition. Preferably, the total amount of the carbosilane monomer is no greater than 60 wt-%, more preferably, no greater than 50 wt-%, and most preferably, no greater than 40 wt-%, based on the total weight of the composition.

Scheme 1 outlines a general procedure for the preparation of a carbosilane-containing material.

Although Scheme 1 is shown using a bis(dimethylsilyl)-arylene, substituents other than methyl can be used in the arylene disilane reactant. Similarly, although Scheme 1 is shown using a methacrylate functional olefin reactant, acrylates can be used as well as other ethylenically unsaturated compounds. Preferably, one of the reactants includes a (meth) acrylate (i.e., acrylate or methacrylate) moiety.

Scheme 1

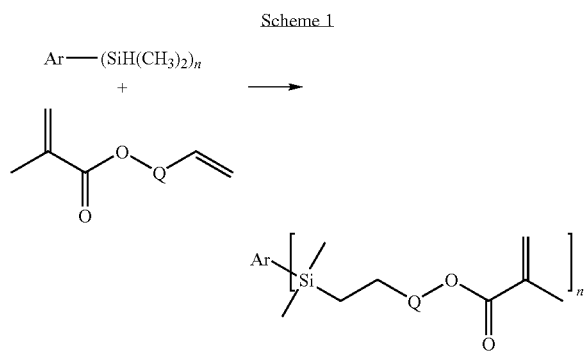

In Scheme 1, Ar, n, and Q are defined above. Although Scheme 1 shows a methacrylate functional olefin reactant, acrylates can be used as well as other ethylenically unsaturated compounds.

As shown in Scheme 1, a multifunctional aromatic silane is reacted with a (meth)acrylate functional ethylenically unsaturated compound through a hydrosilation reaction, resulting in a monomeric product.

Typically, the starting aromatic silane and (meth)acrylate functional ethylenically unsaturated starting materials and a hydrosilation catalyst are reacted together in a solvent, typically at room temperature. The catalyst can then be removed by filtration through silica gel to give the product, or the product can be obtained via crystallization or precipitation.

The hydrosilation catalyst used in the reaction can be any compound that will catalyze the addition reaction of silicon-bonded hydrogen atoms with compounds containing olefinic double bonds. Examples of hydrosilation catalysts suitable for the composition of this invention include many of the late transition elements, such as cobalt, rhodium, iridium, nickel, palladium, and platinum, and their organometallic complexes. Preferred catalysts are those containing the metal platinum, such as finely divided platinum metal, platinum metal on a finely divided carrier, such as charcoal or alumina, and compounds of platinum, such as chloroplatinic acid, platinum olefin complexes, such as those described in U.S. Pat. No. 3,159,601; platinum alkyne complexes, such as those described in U.S. Pat. No. 4,603,215; the reaction product of chloroplatinic acid with a member selected from the class consisting of alcohols, ethers, aldehydes, and mixtures thereof, such as those described in U.S. Pat. No. 3,220,972; and the reaction product of chloroplatinic acid with tetravinylcyclotetrasiloxanes in the presence of sodium bicarbonate in ethanol solution, such as those described in U.S. Pat. No. 3,715,334. Particularly preferred catalysts are the complexes prepared with chloroplatinic acid and certain unsaturated organosilicon compounds, such as those described in U.S. Pat. Nos. 3,419,593; 3,775,452; 4,288,345; and 4,421,903. One specific example of these catalysts is the reaction product of chloroplatinic acid and sym-divinyltetramethyldisiloxane. Another particularly preferred catalyst is a colloidal hydrosilation catalyst obtained by the reaction between a silicon hydride or a siloxane hydride and a platinum(0) or platinum (II) complex, such as those described in U.S. Pat. No. 4,705,765. Still other particularly preferred catalysts are those that are activated by actinic radiation, such as the ($\eta^4$-1,5-cyclooctadiene) diarylplatinum and the ($\eta^5$-cyclopentadienyl) trialiphaticplatinum complexes described in U.S. Pat. Nos. 4,530,879; 4,510,094; and 4,600,484.

The catalyst should be present in an effective amount, i.e., an amount sufficient to catalyze the hydrosilation reaction. Satisfactory results may be obtained when the catalyst is present in an amount sufficient to provide as little as one part by weight of metal (e.g., platinum) per million parts by weight of the total composition. On the other hand, an amount of the catalyst sufficient to provide as high as 1 part to 10 parts by weight of metal (e.g., platinum) per 1,000 parts by weight of the total composition may also be used. In general, however, it is preferred to employ the catalyst in an amount sufficient to provide one to two hundred parts by weight of metal (e.g., platinum) per one million parts by weight of the total composition.

The silane starting material can typically be prepared via the Grignard reaction between halogenated aromatic compounds and chloro-dimethyl silane (or other chloro-alkyl silanes) as disclosed in H. N. Beck et al., *J. Chem. Eng. Data*, 8, 453 (1963).

The ethylenically unsaturated (meth)acrylate components preferably contain one olefin group and at least one (meth) acrylate group. Preferred such compounds include allyl methacrylate, 2-(5/6-methacryloyloxy-bicyclo[2.2.1]hept-2-yl)-ethene, and (2-allyloxyethyl)methacrylate.

Preferred monomers are listed below in Table 1.

TABLE 1

| Structure | Acronym | Viscosity centipoise (cP) | Molecular Weight (MW) |
|---|---|---|---|
| 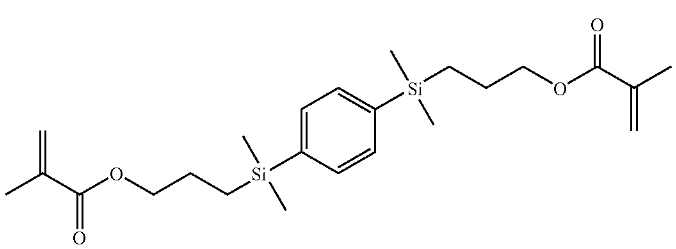 | p-PDA | 136 | 446.74 |

TABLE 1-continued

| Structure | Acronym | Viscosity centipoise (cP) | Molecular Weight (MW) |
|---|---|---|---|
| 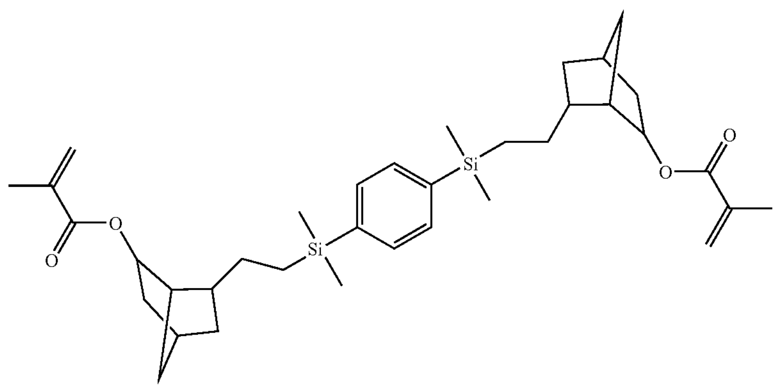 | p-PDN | 7411 | 603.06 |
| 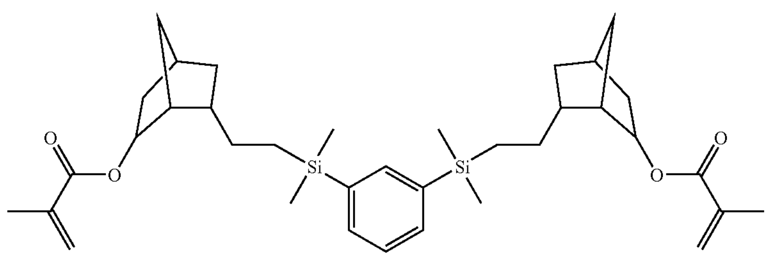 | m-PDN | 3879 | 603.06 |
| 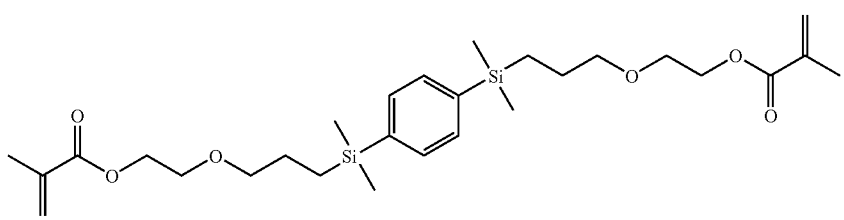 | p-PDE | 32 | 534.85 |
| 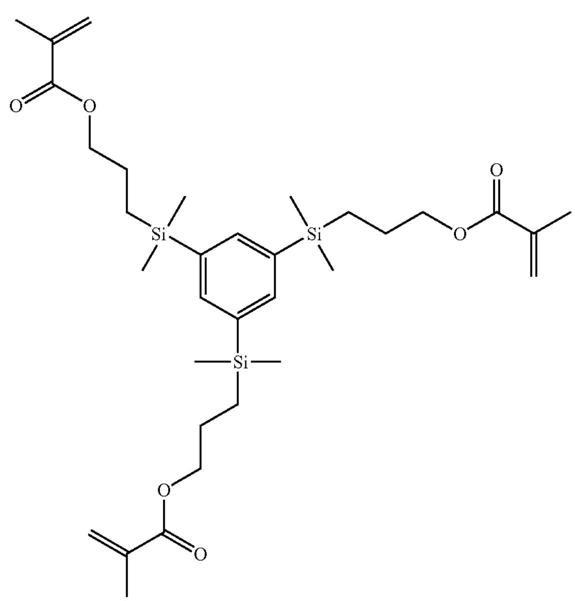 | PTA | 127 | 631.05 |

Secondary Polymerizable Materials

Additional polymerizable components other than the carbosilane monomer disclosed herein can be added to the dental compositions of the present invention. These polymerizable components include one or more hardenable organic resins capable of forming a hardened material having sufficient strength and hydrolytic stability to render them suitable for use in the oral environment. Preferably, at least some of the secondary polymerizable components include ethylenic unsaturation and are capable of undergoing addition polymerization. A suitable secondary polymerizable component preferably includes at least one ethylenically unsaturated monomer (i.e., includes at least one carbon-carbon double bond).

The secondary polymerizable components of the present invention can be part of a hardenable resin. These resins are generally thermosetting materials capable of being hardened to form a polymer network including, for example, acrylate-functional materials, methacrylate-functional materials, vinyl-functional materials, and mixtures thereof. Typically, the hardenable resin is made from one or more matrix-forming oligomers, monomers, polymers, or blends thereof.

One class of hardenable resins includes materials having polymerizable components with free radically active functional groups. Examples of such materials include monomers having one or more ethylenically unsaturated groups, oligomers having one or more ethylenically unsaturated groups, polymers having one or more ethylenically unsaturated groups, and combinations thereof.

In the class of hardenable resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); copolymerizable mixtures of acrylated monomers such as those in U.S. Pat. No. 4,652,274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0 373 384 (Wagenknecht et al.), EP-0 201 031 (Reiners et al.), and EP-0 201 778 (Reiners et al.). Mixtures of two or more free radically polymerizable compounds can be used if desired.

The secondary polymerizable component may also contain hydroxyl groups and free radically active functional groups in a single molecule. Examples of such materials include hydroxyalkyl(meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. Mixtures of ethylenically unsaturated compounds can be used if desired.

The above-listed components are typically noncrystallizable (i.e., amorphous). The secondary polymerizable component can also include a crystallizable component. This crystallizable component may or may not have a reactive group capable of polymerizing and/or crosslinking. Preferably, the crystallizable component is polymerizable. Preferably, the crystallizable component is polymeric (including oligomeric). More preferably, the crystallizable component is a polymerizable polymeric material. The secondary crystallizable polymers (including oligomers) suitable for use in the dental composition can have crystallizable main chain (i.e., linear) or pendant (i.e., side chain) segments. Preferred materials also contain reactive groups capable of polymerizing and/or crosslinking. Especially preferred are non-carbosilane crystallizable oligomers or prepolymers with a reactive functionality of at least two.

Examples of suitable secondary crystallizable materials having crystallizable main chain or backbone segments include, but are not limited to, polyesters (including polycaprolactones), polyethers, polythioethers, polyarylalkylenes, polysilanes, polyamides, polyolefins (preferably, formed from lower, e.g., C2-C3 olefins), and polyurethanes.

Preferred secondary crystallizable materials are saturated, linear, aliphatic polyester polyols (particularly diols) containing primary hydroxyl end groups. Examples of commercially available materials useful as the non-carbosilane crystallizable component in the dental compositions of the invention include some resins available under the trade designation LEXOREZ from Inolex Chemical Co., Philadelphia, Pa. Examples of other polyester polyols useful in the compositions of the invention are those available under the trade designation RUCOFLEX from Ruco Polymer Corp., Hicksville, N.Y. Examples of polycaprolactones that are useful in the invention include those available under the trade designations TONE 0230, TONE 0240, and TONE 0260 from Dow Chemical Co., Midland, Mich. Especially preferred materials are saturated, linear, aliphatic polyester polyols that are modified (e.g., through primary hydroxyl end groups) to introduce polymerizable, unsaturated functional groups, e.g., polycaprolactone diol reacted with 2-isocyanatoethyl methacrylate, methacryloyl chloride, or methacrylic anhydride.

Preferably, the total amount of the secondary polymerizable component is no greater than 60 wt-%, more preferably, no greater than 50 wt-%, and most preferably, no greater than 40 wt-%, based on the total weight of the composition.

Initiator System

Compositions of the present invention can optionally include an initiator system, i.e., one initiator or a mixture of two or more initiators, which are suitable for hardening (e.g., polymerizing and/or crosslinking) the resin system (e.g., the carbosilane-containing monomer and (meth)acrylate component). The initiator system preferably includes free radical initiators, which may be activated in a variety of ways, e.g., heat and/or radiation. Thus, for example, the initiator system can include a thermal initiator (e.g., azo compounds and peroxides), or a photoinitiator.

Preferably, the initiator system includes one or more photoinitiators. More preferably, the initiator system includes at least one photoinitiator active in the spectral region of 300 nanometers (nm) to 1200 nm and capable of promoting free radical polymerization and/or crosslinking of ethylenically unsaturated moieties upon exposure to light of suitable wavelength and intensity. A wide variety of such photoinitiators can be used. The photoinitiator preferably is soluble in the resin system. Preferably, the photoinitiator is sufficiently shelf stable and free of undesirable coloration to permit storage and use under typical dental operatory and laboratory conditions. Visible light photoinitiators are preferred.

One type of suitable initiator (i.e., initiator system) is described in U.S. Pat. No. 5,545,676 (Palazzotto et al.), which includes a three-component or ternary photoinitiator system. This system includes an iodonium salt, e.g., a diaryliodonium salt, which can be a simple salt (e.g., containing an anion such as Cl-, Br—, I—, or $C_2H_5SO_3$—) or a metal complex salt (e.g., containing $SbF_5OH$ or $AsF_6$—). Mixtures of iodonium salts can be used if desired. The second component in this ternary photoinitiator system is a sensitizer, which is capable of light absorption within the range of wavelengths of 400 nm to 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyamide, ascorbic acid and its salts, dithiocarbamic acid and its salts, salts of xanthates, salts of ethylene diamine tetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha diketones), ketocoumarins, aminoarylketones, and p-substituted aminostyryl ketone compounds are preferred sensitizers. Examples of particularly preferred visible light sensitizers include camphorquinone, glyoxal, biacetyl, 3,3,6,6 tetramethylcyclohexanedione, 3,3,7,7-tetramethyl-1,2-cycloheptanedione, 3,3,8,8-tetramethyl-1,2-cyclooctanedione, 3,3,18,18-tetramethyl-1,2 cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4 heptanedione, 2,3-octanedione, 4,5-octanedione, and 1,2-cyclohexanedione. Of these, camphorquinone is the most preferred sensitizer.

Yet another type of photoinitiator includes acylphosphine oxides, such as those described in European Pat. Application No. 173567 (Ying). Suitable acylphosphine oxides are preferably of the general formula $(R^4)_2$—P(=O)—C(=O)—$R^5$, wherein each $R^4$ is individually a hydrocarbon group, preferably an alkyl group, alicyclic group, aryl group, and aralkyl group, any of which can be substituted with a halo-, alkyl- or alkoxy-group, or the two $R^4$ groups can be joined to form a ring along with the phosphorous atom, and wherein $R^5$ is a hydrocarbon group, preferably, a S—, O—, or N-containing five- or six-membered heterocyclic group, or a -Z-C(=O)—P(=O)—$(R^4)_2$ group, wherein Z represents a divalent hydrocarbon group such as alkylene or phenylene having from 2 to 6 carbon atoms. Examples of suitable acylphosphine oxides include bis(2,4,6 trimethylbenzoyl)phenyl phosphine oxide, for example. Optionally, tertiary amine reducing agents may be used in combination with an acylphosphine oxide. Illustrative tertiary amines useful in the invention include those described above as well as ethyl 4-(N,N-dimethylamino)benzoate and N,N-dimethylaminoethyl methacrylate.

Mono- and all-ketones can also be used as photoinitiators. Examples of such systems are described in U.S. Pat. No. 4,071,424 (Dart et al.).

Still another class of photoinitiators includes ionic dye-counterion complex initiators that include a borate anion and a complementary cationic dye. Borate anions useful in these photoinitiators generally can be of the formula $B(R^6)_4$— wherein each $R^6$ is independently an alkyl, aryl, alkaryl, allyl, aralkyl, alkenyl, alkynyl, alicyclic, and saturated or unsaturated heterocyclic groups. Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. Quaternary ammonium groups useful as counterions can be trimethylcetylammonium, cetylpyridinium, and tetramethylammonium. Other organophilic cations can include pyridinium, phosphonium, and sulfonium. Cationic transition metal coordination complexes that may be useful as counterions can be complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Borate salt photoinitiators are described, for example, in U.S. Pat. Nos. 4,772,530 (Gottschalkea et al.), 4,954,414 (Adair et al.), 4,874,450 (Gottschalkea), 5,055,372 (Shanklin et al.), and 5,057,393 (Shanklin et al.).

Preferred visible light-induced initiators include camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. Particularly preferred visible light-induced photoinitiators include combinations of an alpha-diketone, e.g., camphorquinone with additional hydrogen donors, and optionally a diaryliodonium salt, e.g., diphenyliodonium chloride, bromide, iodide or hexafluorophosphate. Preferred ultraviolet light-induced polymerization initiators include ketones, such as benzyl and benzoin, acyloins, and acyloin ethers. Preferred ultraviolet light-induced polymerization initiators include 2,2-dimethoxy-2-phenylacetophenone available under the trade designation IRGACURE 651 and benzoin methyl ether (2-methoxy-2-phenylacetophenone), both from Ciba Speciality Chemicals Corp., Tarrytown, N.Y.

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the composition. Preferably, the initiator system is present in a total amount of no more than 10 wt-%, more preferably, no more than 5 wt-%, and most preferably, no more than 2.5 wt-%, based on the weight of the composition.

Filler System

Compositions of the present invention can optionally include a filler system (i.e., one or more fillers). Fillers for use in the filler system may be selected from a wide variety of conventional fillers for incorporation into resin systems. Preferably, the filler system includes one or more conventional materials suitable for incorporation in compositions used for medical applications, for example, fillers currently used in dental restorative compositions. Thus, the filler systems used in the compositions of the present invention are incorporated into the resin systems.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Preferred particulate filler is finely divided and has an average particle size (preferably, diameter) of less than 10 micrometers (i.e., microns).

Preferred micron-size particulate filler has an average particle size of at least 0.2 micron up to 1 micrometer. Nanoscopic particles have an average primary particle size of less than 200 nm (0.2 micron). The filler can have a unimodal or polymodal (e.g., bimodal) particle size distribution.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks. Materials of this type ("nanoscopic" materials) have average primary particle sizes (i.e., the largest dimension, e.g., diameter, of unaggregated material) of no greater than 1000 nanometers (nm). Preferably, the nanoscopic particulate material has an average primary particle size of at least 2 nanometers (nm), and preferably at least 7 nm. Preferably, the nanoscopic particulate material has an average primary particle size of no greater than 50 nm, and more preferably no greater than 20 nm in size. The average surface area of such a filler is preferably at least 20 square meters per gram ($m^2/g$), more preferably, at least 50 $m^2/g$, and most preferably, at least 100 $m^2/g$.

The filler system can include an inorganic material. It can also include a crosslinked organic material that is insoluble in the polymerizable resin, and is optionally filled with inorganic filler. The filler system is preferably generally non-toxic and suitable for use in the mouth.

Suitable fillers can be radiopaque, radiolucent, or nonradiopaque. Fillers as used in dental applications are typically ceramic in nature. Examples of suitable inorganic fillers are naturally occurring or synthetic materials such as quartz; nitrides (e.g., silicon nitride), glasses derived from, for example Ce, Sb, Sn, Zr, Sr, Ba, or Al, colloidal silica, feldspar, borosilicate glass, kaolin, talc, titania, and zinc glass, zirconia-silica fillers; and low Mohs hardness fillers such as those described in U.S. Pat. No. 4,695,251 (Randklev). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169 (Randklev). Mixtures of these fillers can also be used, as well as combination fillers made from organic and inorganic materials.

Optionally, the surface of the filler particles may be treated with a surface treatment, such as a silane-coupling agent, in order to enhance the bond between the filler system and the resin system. The coupling agent may be functionalized with reactive curing groups, such as acrylates, methacrylates, and the like.

The filler particles used to impart a noncovalent structure can be composed of silica, alumina, zirconia, titania, or mixtures of these materials with each other or with carbon. In their synthesized state, these materials are commonly hydrophilic, due to the presence of surface hydroxyl groups. However, the materials may also be modified by treatment with appropriate agents, such as alkyl silanes, in order to modify this character. For example, the surface of a filler particle may be rendered neutral, hydrophobic, or reactive, depending on the desired properties. Fumed silica is a preferred compound for imparting self-supporting character, due to its low cost, commercial availability, and wide range of available surface character.

Other suitable fillers are disclosed in U.S. Pat. Nos. 6,387,981 (Zhang et al.) and 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. patent applications entitled, "Dental Compositions Containing Nanozirconia Fillers," U.S. Ser. No. 10/847,782; "Dental Compositions Containing Nanofillers and Related Methods," U.S. Ser. No. 10/847,781; and "Use of Nanoparticles to Adjust Refractive Index of Dental Compositions," U.S. Ser. No. 10/847,803 all three of which were filed on May 17, 2004.

Preferably, the total amount of filler system is greater than 50 wt-%, more preferably, greater than 60 wt-%, and most preferably, greater than 70 wt-%, based on the total weight of the composition. If the filler system includes fibers, the fibers are present in an amount of less than 20 wt-%, based on the total weight of the composition. Preferably, the total amount of filler system is no more than 95 wt-%, and more preferably, no more than 80 wt-%, based on the total weight of the composition.

Optional Additives

The compositions of the invention may contain a surfactant system, i.e., one surfactant or a mixture of two or more surfactants. Such surfactants can be nonionic, anionic, or cationic. The surfactant(s) can be copolymerizable or non-copolymerizable.

The composition may additionally include optional agents such as colorants (e.g., pigments or dyes conventionally used for shade adjustment), flavoring agents, medicaments, stabilizers (such as Butylated Hydroxy Toluene (BHT)), viscosity modifiers, diluting agents, flow control additives, thixotropic agents, antimicrobials, polymeric thickeners, and the like. Various combinations of these optional additives can be used if desired. Such agents may optionally include reactive functionality so that they will be copolymerized with the resin.

Preferably, the total amount of optional component is no more than 5.0 wt-%, more preferably, no more than about 2.5 wt-%, and most preferably, no more than 1.5 wt-%, based on the total weight of the composition.

Method of Use

The above described carbosilane-containing monomer can be used as a component in dental compositions that are hardenable, preferably via radical polymerization of unsaturated groups, especially (meth)acrylate groups. Dental compositions of the present invention can be used, for example, as dental restoratives or prefabricated prosthetic devices. Examples of restoratives include dental composites and amalgams. Examples of prefabricated prosthetic devices include crowns, bridges, veneers, inlays, onlays, posts, pins, and the like.

The compositions of the present invention can also be shaped (e.g., molded) into a variety of forms like three-dimensional shapes, preformed sheets, arch shaped trays, ropes, buttons, woven, or non-woven webs, and the like. The composition can be shaped (to form a first shape) in a variety of ways including, for example, extruding, injection molding, compression molding, thermoforming, vacuum forming, pressing, calendering, and web processing using rollers. Typically, a semi-finished shape is formed using a mold with a positive and negative impression. The shaped forms can be used, for example, as dental crowns, dental impression trays, and orthodontic appliances. Examples of orthodontic appliances include lingual retainers, space retainers, hooks, buttons, splints, and bases for orthodontic brackets.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

Compressive Strength (CS) Test Method

Compressive strength of a test sample was measured according to American National Standards Institute/American Standards Association (ANSI/ASA) specification No. 27 (1993). A sample was packed into a 4 millimeters (mm) (inside diameter) glass tube (and if necessary the sample was heated to accomplish the packing), and the tube was capped with silicone rubber plugs and compressed axially at approximately 0.28 megapascal (Mpa) for 5 minutes. The sample was then light cured for 90 seconds by exposure to two oppositely disposed VISILUX Model 2500 blue light guns (3M Co., St. Paul, Minn.) followed by irradiation for 180 seconds in a Dentacolor XS unit (Kulzer, Inc., Germany). Cured samples were cut with a diamond saw to form 8-mm long cylindrical plugs for measurement of compressive strength. The plugs were stored in distilled water at 37° C. for 24 hours prior to testing. Measurements were carried out on an Instron tester (Instron 4505, Instron Corp., Canton, Mass.) with a 10 kilonewton (kN) load cell at a crosshead speed of 1 mm/minute. Five cylinders of cured samples were prepared and measured with the results reported in MPa as the average of the five measurements.

Diametral Tensile Strength (DTS) Test Method

Diametral tensile strength of a test sample was measured according to ANSI/ASA specification No. 27 (1993). A sample was compressed into a glass tube and cured as described for the CS Test Method. The cured sample was then cut into 2,2-mm thick disks for measurement of DTS. The disks were stored in water as described above and measured with an Instron tester (Instron 4505, Instron Corp.) with a 10 (kN) load cell at a crosshead speed of 1 mm/minute. Five disks of cured samples were prepared and measured with results reported in MPa as the average of the five measurements.

Polymerization Shrinkage Test Method

The polymerization shrinkage of a test sample was measured using the Watts shrinkage test procedure (D. C. Watts et al., *Meas. Sci. Technol.*, 2, 788-794 (1991)). The test was performed using a 3-mm glass slide.

Viscosity Test Method

The viscosity of a test sample was measured using an AR 2000 Rheometer (TA Instruments, New Castle, Del.). Approximately 1.2 gram (g) of sample was placed between the stage (at 25° C.) and a 40-mm aluminum plate. The plate was rotated according to a stepped flow procedure with a log shear stress ramp from 1 to 1000 Pa (total of 10 data points). The viscosity results were reported in centipoise (cP) at 25° C. as the average of the 10 data points.

Abbreviations, Descriptions, and Sources of Materials

| Abbreviation | Description and Source of Material |
| --- | --- |
| BHT | 2,6-di-tert-butyl-4-methylphenol (Sigma-Aldrich, St. Louis, MO) |
| BisGMA | 2,2-Bis[4-(2-hydroxy-3-methacryloyloxypropoxy)phenyl]propane CAS No. 1565-94-2 |
| CPQ | Camphorquinone (Sigma-Aldrich) |
| EDMAB | Ethyl 4-(N,N-dimethylamino)benzoate (Sigma-Aldrich) |
| STZ | Silane-treated zirconia-silica filler prepared as described in U.S. Pat. No. 6,624,211 (Karim) |
| UDMA | Diurethane dimethacrylate (ROHAMERE 6661-0, Monomer Polymer & Dajac Labs, Inc., Feasterville, PA) |
| BisEMA-6 | Six-mole ethoxylated bisphenol A dimethacrylate (Sartomer CD541, Sartomer Co., Exton, PA) |
| DPIHFP | Diphenyl Iodonium Hexafluorophosphate (Johnson Matthey, Alpha Aesar Division, Ward Hill, NJ) |
| Benzotriazole | 2-(2-Hydroxy-5-methacryloxyethylphenyl)-2H-benzotriazole (Ciba Specialty Chemicals, Tarrytown, NJ) |
| TEGDMA | Triethyleneglycol dimethacrylate (Sigma-Aldrich) |

Example 1

Synthesis of 1,4-bis-(dimethyl-[3-(methacryloyloxy)propyl]silyl)benzene (p-PDA)

A mixture of 1,4-bis-dimethylsilylbenzene (Gelest, Tulleytown, Pa.) (5.00 g, 25.7 millmole (mmol)), allyl methacrylate (Sigma-Aldrich) (6.49 g, 51.4 mmol), toluene (20 milliliter (ml)), and two drops of a solution of platinum-divinyltetramethyldisiloxane complex in xylene (Gelest) was mixed at room temperature for 17 hours. The resulting mixture was loaded onto a silica gel column and eluted with a mixture of ethyl acetate (20 volume percent (vol %)) in hexane (80 vol %). The solvent was evaporated to yield the product as a colorless oil (7.80 g) having a MW of 446.74 and a viscosity of 136 cP. Characterization of the oil by 1H Nuclear Magnetic Resonance Spectroscopy (NMR) and Infrared Spectroscopy (IR) spectra was consistent with the p-PDA structure.

Example 2

Synthesis of 1,4-bis-(dimethyl-[2-(5/6-methacryloyloxy-bicyclo[2.2.1]hept-2-yl)-ethyl]silyl)benzene (p-PDN)

A mixture of 1,4-bis-dimethylsilylbenzene (3.77 g, 19.4 mmol), 2-(5/6-methacryloyloxy-bicyclo[2.2.1]hept-2-yl) ethene (prepared according to Example 14 in U.S. Pat. No. 3,927,116 (Rick et al.)) (8.00 g, 38.8 mmol), toluene (15 ml), and two drops of a solution of platinum-divinyltetramethyldisiloxane complex in xylene was mixed at room temperature for 24 hours. The resulting mixture was loaded onto a silica gel column and eluted with a mixture of ethyl acetate (30 vol %) in hexane (70 vol %). The solvent was evaporated to yield the product as a colorless oil (11.07 g) having a MW of 603.06 and a viscosity of 7411 cP. Characterization of the oil by 1H NMR and IR spectra was consistent with the p-PDN structure.

Example 3

Synthesis of 1,3-bis-(dimethyl-[2-(5/6-methacryloyloxy-bicyclo[2.2.1]hept-2-yl)-ethyl]silyl)benzene (m-PDN)

A solution of 1,3-dibromobenzene (Sigma-Aldrich) (30.00 g, 0.13 mole (mol)) in dry tetrahydrofuran (65 ml) was added dropwise over one hour to a mixture of chlorodimethylsilane (Sigma-Aldrich) (40.10 g, 0.42 mol), dry tetrahydrofuran (100 ml), and magnesium turnings (24.31 g, 0.13 mol). After full addition, the mixture was refluxed for 2 hours. The solvent was then removed under vacuum and the residue was diluted with hexane (200 ml). The solid was washed two times with hexane (200 ml) and filtered. The combined hexane solutions were concentrated under vacuum, and the residue was distilled under reduced pressure (47-49° C. at 2 mm Hg, 267 Pascals) to yield 1,3-bis-dimethylsilylbenzene as a colorless oil (17.41 g).

A mixture of 1,3-bis-dimethylsilylbenzene (3.77 g, 19.4 mmol), 2-(5/6-methacroyloxy-bicyclo[2.2.1]hept-2-yl) ethene (8.00 g, 38.8 mmol), toluene (20 ml), two drops of a solution of platinum-divinyltetramethyldisiloxane complex in xylene was mixed at room temperature for 17 hours. The mixture was loaded onto a silica gel column and eluted with a mixture of ethyl acetate (30 vol %) in hexane (70 vol %). The solvent was evaporated to yield the product as a colorless oil (9.52 g) having a Molecular Weight (MW) of 603.06 and a viscosity of 3879 cP. Characterization of the oil by 1H NMR and IR spectra was consistent with the m-PDN structure.

Example 4

Synthesis of 1,3,5-tris-(dimethyl-[3-(methacroyloxy) propyl]silyl)benzene (PTA)

A mixture of chlorodimethylsilane (47.30 g, 0.50 mol), dry tetrahydrofuran (150 ml), and magnesium turnings (12.20 g, 0.50 mol) was stirred for one hour, followed by dropwise addition of a solution of 1,3,5-tribromobenzene (Sigma-Aldrich) (31.50 g, 0.10 mol) in dry tetrahydrofuran (100 ml) over one hour. After full addition, the mixture was refluxed for 4 hours and then stirred for 17 hours at room temperature. The solution was decanted from the solids that had precipitated and the solids were further washed and filtered three times with hexane (200 ml). The combined organic solutions were concentrated under vacuum, and the residue was distilled under reduced pressure (65-68° C. at 0.2 mm Hg, 27 Pascals) to yield 1,3,5-tris-dimethylsilyl benzene as a colorless oil (12.01 g).

A mixture of 1,3,5-tris-dimethylsilyl benzene (3.00 g, 11.9 mmol), allyl methacrylate (4.50 g, 35.6 mmol), toluene (15 ml), and three drops of a solution of platinum-divinyltetramethyldisiloxane complex in xylene was mixed at room temperature for 48 hours. The mixture was loaded onto a silica gel column and eluted with a mixture of ethyl acetate (20 vol %) in hexane (80 vol %). The solvent was evaporated to yield the product as a colorless oil (4.10 g) having a MW of 631.05 and a viscosity of 127 cP. Characterization of the oil by 1H NMR and IR spectra was consistent with the PTA structure.

Example 5

Synthesis of 1,4-bis-(dimethyl-[3-(2-methacryloyloxyethyloxy)propyl]silyl)benzene (p-PDE)

A mixture of 1,4-bis-dimethylsilyl benzene (2.86, 15 mmol), 2-allyloxyethyl methacrylate (Monomer-Polymer & Dajac Labs, Inc., Feasterville, Pa.) (5.00 g, 30 mmol), toluene (15 ml), and two drops of a solution of platinum-divinyltetramethyldisiloxane complex in xylene was mixed at room temperature for 24 hours. The mixture was loaded onto a silica gel column and eluted with a mixture of ethyl acetate (20 vol %) in hexane (80 vol %). The solvent was evaporated to yield the product as a colorless oil (6.45 g) having a MW of 534.85 and a viscosity of 32 cP. Characterization of the oil by 1H NMR and IR spectra was consistent with the p-PDE structure.

Examples 6-32

Polymerizable Compositions

Polymerizable compositions (Examples 6-32) were prepared according to the following general procedure. The photoinitiator/stabilizer components were initially dissolved in BisGMA and the resulting mixture combined with the other monomer components of the composition (BisEMA-6, UDMA, TEGDMA, and Carbosilane (selected from Examples 1-5)). The concentrations of photoinitiator/stabilizer components used (in terms of parts per hundred parts of BisGMA (i.e., resin), phr) were CPQ (0.176 phr), EDMAB (1.55 phr), DPIHFP (0.517 phr), BHT (0.155 phr), and Benzotriazole (1.552 phr). The blended monomer components plus the filler component STZ were weighed into a MAX 20 plastic mixing cup having a screw cap (Flakteck, Landrum, S.C.) and then the closed cup heated in an oven at 85° C. for 30 minutes. The cup was placed in a DAC 150 FV speed mixer (Flakteck) and spin mixing was carried out for 1 minute at 3000 rpm. The cup was then reheated for 30 minutes at 85° C. followed by another minute of mixing at 3000 rpm to yield the final blended compositions. The amounts of components for each example are provided in Table 1. The weight of BisGMA in Table 1 includes the weight of the photoinitiator/stabilizer components.

TABLE 1

| Ex. | Carbosilane Monomer (Example) | Carbosilane Monomer (g) | BisGMA (g) | BisEMA-6 (g) | UDMA (g) | TEGDMA (g) | STZ (g) |
| --- | --- | --- | --- | --- | --- | --- | --- |
| 6 | 1 | 0.42 | 0.98 | 0 | 0 | 0 | 5.60 |
| 7 | 1 | 0.84 | 0.56 | 0 | 0 | 0 | 5.60 |
| 8 | 1 | 0.70 | 0.70 | 0 | 0 | 0 | 5.60 |
| 9 | 1 | 0.42 | 0.56 | 0 | 0.42 | 0 | 5.60 |
| 10 | 1 | 0.56 | 0.42 | 0 | 0.56 | 0 | 5.60 |
| 11 | 1 | 0.15 | 0.31 | 0.45 | 0.45 | 0.06 | 6.38 |
| 12 | 1 | 0.28 | 0.28 | 0.40 | 0.40 | 0.06 | 6.38 |
| 13 | 1 | 0.42 | 0.25 | 0.34 | 0.34 | 0.05 | 6.38 |
| 14 | 2 | 0.14 | 0.32 | 0.54 | 0.44 | 0.06 | 6.38 |
| 15 | 2 | 0.28 | 0.28 | 0.41 | 0.39 | 0.06 | 6.38 |
| 16 | 2 | 0.42 | 0.25 | 0.36 | 0.34 | 0.05 | 6.38 |
| 17 | 2 | 0.50 | 0.42 | 0 | 0.42 | 0.07 | 6.38 |
| 18 | 2 | 0.56 | 0.21 | 0.30 | 0.30 | 0.05 | 6.38 |
| 19 | 2 | 0.70 | 0.18 | 0.25 | 0.25 | 0.04 | 6.38 |
| 20 | 3 | 0.28 | 0.28 | 0.40 | 0.40 | 0.06 | 6.37 |
| 21 | 3 | 0.42 | 0.25 | 0.35 | 0.34 | 0.05 | 6.38 |
| 22 | 3 | 0.56 | 0.21 | 0.29 | 0.30 | 0.04 | 6.38 |
| 23 | 3 | 0.42 | 0.35 | 0.21 | 0.30 | 0.14 | 6.38 |
| 24 | 3 | 0.44 | 0.42 | 0.14 | 0.22 | 0.21 | 6.38 |
| 25 | 3 | 0.45 | 0.21 | 0.21 | 0.50 | 0.07 | 6.38 |
| 26 | 4 | 0.14 | 0.32 | 0.45 | 0.44 | 0.06 | 6.38 |
| 27 | 4 | 0.28 | 0.28 | 0.40 | 0.40 | 0.06 | 6.38 |
| 28 | 4 | 0.43 | 0.25 | 0.35 | 0.35 | 0.05 | 6.38 |
| 29 | 4 | 0.49 | 0.42 | 0 | 0.43 | 0.07 | 6.38 |
| 30 | 5 | 0.28 | 0.28 | 0.40 | 0.40 | 0.06 | 6.38 |
| 31 | 5 | 0.42 | 0.25 | 0.35 | 0.34 | 0.05 | 6.38 |
| 32 | 5 | 0.56 | 0.84 | 0 | 0 | 0 | 6.38 |

Evaluation of Composition Properties

Composition samples (Examples 6-32) were evaluated for polymerization shrinkage, compressive strength, and diametral tensile strength according to the Test Methods described herein. Results are provided in Table 2.

TABLE 2

| Example | Shrinkage (vol %) | Compressive Strength, MPa (Standard Deviation) | Diametral Tensile Strength, MPa (Standard Deviation) |
| --- | --- | --- | --- |
| 6 | 1.60 | 331 (12) | 75 (8) |
| 7 | 1.78 | 326 (8) | 78 (3) |
| 8 | 1.74 | 312 (5) | 64 (17) |
| 9 | 1.71 | 311 (15) | 58 (6) |
| 10 | 1.82 | 347 (28) | 71 (13) |
| 11 | 1.88 | 340 (27) | 74 (9) |
| 12 | 1.85 | 341 (27) | 83 (7) |
| 13 | 1.90 | 337 (22) | 80 (18) |
| 14 | 1.79 | 324 (33) | 85 (10) |
| 15 | 1.66 | 354 (20) | 83 (12) |
| 16 | 1.57 | 358 (21) | 91 (12) |
| 17 | 1.43 | 313 (15) | 80 (7) |
| 18 | 1.45 | 305 (15) | 81 (8) |
| 19 | 1.41 | 316 (23) | 72 (4) |
| 20 | 1.60 | 327 (23) | 84 (10) |
| 21 | 1.44 | 340 (39) | 81 (7) |
| 22 | 1.43 | 312 (22) | 77 (9) |
| 23 | 1.71 | 307 (51) | 85 (9) |
| 24 | 1.81 | 322 (11) | 77 (6) |
| 25 | 1.66 | 319 (13) | 84 (3) |
| 26 | 1.75 | 338 (44) | 91 (14) |
| 27 | 1.72 | 319 (42) | 81 (7) |
| 28 | 1.64 | 300 (47) | 80 (6) |
| 29 | 1.68 | 344 (22) | 83 (7) |
| 30 | 1.70 | 333 (18) | 83 (7) |
| 31 | 1.77 | 343 (22) | 88 (9) |
| 32 | 1.41 | 328 (26) | 85 (6) |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A dental composition comprising:
   a polymerizable carbosilane-containing monomer wherein the carbosilane-containing monomer has the following (Formula I):

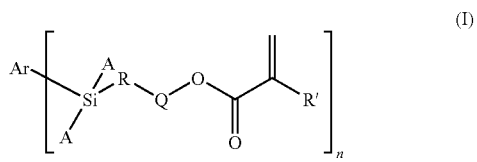

wherein:
   Ar is an arylene group;
   each A is independently an aliphatic, cycloaliphatic, aromatic group, or combinations thereof;
   each R is independently an aliphatic group, cycloaliphatic group, or combinations thereof, optionally including one or more O, Br, Cl, or Si atoms, or combinations thereof, which can include a bicyclic group;
   each Q is independently a bond, or an aliphatic group, cycloaliphatic group, aromatic group, or combinations thereof, optionally including one or more O, Br, Cl, or Si atoms, or combinations thereof, which can include a bicyclic group;

each R' is independently hydrogen or methyl; and
n is at least two; and
a polymerizable (meth)acrylate component different from the carbosilane-containing monomer.

2. The dental composition of claim 1 further comprising a filler system.

3. The dental composition of claim 1 further comprising an initiator system.

4. The dental composition of claim 1 further comprising an additive selected from the group consisting of a colorant, a flavoring agent, a medicament, a stabilizer, a viscosity modifier, a diluting agent, a flow control additive, a thixotropic agent, a polymeric thickener, an antimicrobial, and combinations thereof.

5. The dental composition of claim 1 having a polymerization shrinkage of no greater than 2.0%, based on the volume of the composition prior to hardening.

6. The dental composition of claim 1 wherein the total amount of the carbosilane monomer in the dental composition is 1 wt-% to 60 wt-%, based on the total weight of the composition.

* * * * *

UNITED STATES PATENT AND TRADEMARK OFFICE
CERTIFICATE OF CORRECTION

PATENT NO. : 7,576,144 B2
APPLICATION NO. : 11/571944
DATED : August 18, 2009
INVENTOR(S) : Lewandowski et al.

It is certified that error appears in the above-identified patent and that said Letters Patent is hereby corrected as shown below:

On Title page Other Publication
Column 2
First page, line 2, delete "Phenenyl" and insert -- Phenyl -- therefore.
Second page, line 9, delete "(Karim)" and insert -- (Karim) (55093USA4A) -- therefore.
Line 11, delete "60/587,978" and insert -- (59880US002) -- therefore.

Column 9
Line 45, delete "hexacrylate," and insert -- hexaacrylate, -- therefore.

Column 11
Line 24, delete "C1-," and insert -- Cl—, -- therefore.
Line 35, delete "ferrocyamide," and insert -- ferrocyanide, -- therefore.
Line 49-50, delete "3,3,6,6 tetramethylcyclohexanedione," and insert
-- 3,3,6,6-tetramethylcyclohexanedione, -- therefore.
Line 52, delete "1,2 cyclooctadecanedione," and insert -- 1,2-cyclooctadecanedione, -- therefore.
Line 54-55, delete "3,4 heptanedione," and insert -- 3,4-heptanedione, -- therefore.

Column 12
Line 5, delete "bis(2,4,6 trimethylbenzoyl)phenyl" and insert
-- bis(2,4,6-trimethylbenzoyl)phenyl -- therefore.

Column 15
Line 65, delete "2,2-mm" and insert -- 2.2-mm -- therefore.

Column 16
Line 57-58, delete "Tulleytown," and insert -- Tullytown, -- therefore.
Line 58, delete "millmole" and insert -- millimole -- therefore.

Signed and Sealed this
Twenty-first Day of June, 2011

David J. Kappos
*Director of the United States Patent and Trademark Office*

CERTIFICATE OF CORRECTION (continued)
U.S. Pat. No. 7,576,144 B2

Column 17
Line 46, delete "methacroyloxy" and insert -- methacryloyloxy -- therefore.
Line 59, delete "(methacroyloxy)" and insert -- (methacryloyloxy) therefore.